(12) United States Patent
Warner et al.

(10) Patent No.: US 10,434,277 B2
(45) Date of Patent: Oct. 8, 2019

(54) POSITIVE EXPIRATORY PRESSURE DEVICE AND METHODS OF USING SAME

(71) Applicants: Christopher D. Warner, Apopka, FL (US); Bradley Allen Wheeler, Greenwood, IN (US)

(72) Inventors: Christopher D. Warner, Apopka, FL (US); Bradley Allen Wheeler, Greenwood, IN (US)

(73) Assignee: RBT MEDICAL PRODUCTS LLC, Apopka, FL (US)

( * ) Notice: Subject to any disclaimer, the term of this patent is extended or adjusted under 35 U.S.C. 154(b) by 1018 days.

(21) Appl. No.: 14/826,410

(22) Filed: Aug. 14, 2015

(65) Prior Publication Data

US 2016/0045690 A1 Feb. 18, 2016

Related U.S. Application Data

(60) Provisional application No. 62/037,569, filed on Aug. 14, 2014.

(51) Int. Cl.
*A61M 16/20* (2006.01)
*A61M 16/08* (2006.01)

(52) U.S. Cl.
CPC ....... *A61M 16/209* (2014.02); *A61M 16/0816* (2013.01); *A61M 2205/586* (2013.01)

(58) Field of Classification Search
CPC ...... A61M 16/209; A61M 16/20; A63B 23/18
See application file for complete search history.

(56) References Cited

U.S. PATENT DOCUMENTS

| | | | |
|---|---|---|---|
| 1,392,700 A | 10/1921 | Oyen | |
| 4,257,453 A * | 3/1981 | Kohnke | A61M 16/208 137/514.3 |
| 4,601,465 A | 7/1986 | Roy | |
| 4,854,574 A * | 8/1989 | Larson | A63B 23/18 128/200.24 |
| 5,547,440 A | 8/1996 | Rubens | |
| D450,381 S | 11/2001 | Weinstein | |
| 6,343,603 B1 | 2/2002 | Tuck | |
| 6,425,393 B1 | 7/2002 | Lurie | |
| 6,500,095 B1 | 12/2002 | Hougen | |
| 6,659,100 B2 | 12/2003 | O'Rourke | |
| 6,726,598 B1 | 4/2004 | Jarvis | |
| 6,848,443 B2 | 2/2005 | Schmidt | |
| 6,904,906 B2 | 6/2005 | Salter | |
| D561,330 S | 2/2008 | Richards | |
| 7,699,054 B2 | 4/2010 | Pelerossi | |

(Continued)

FOREIGN PATENT DOCUMENTS

WO WO22000027455 A1 5/2000

*Primary Examiner* — Jan Christopher L Merene
*Assistant Examiner* — Cana A Gallegos
(74) *Attorney, Agent, or Firm* — FisherBroyles LLP; Anthony J. DoVale (57) ABSTRACT

A hand-held positive expiratory pressure device is presented. A float is insertable into an internal chamber of a housing and is urged towards a sealing surface by a biasing member to restrict or prevent airflow through the internal chamber. A user exhaling through the device urges the float away from the sealing surface to allow fluid to flow through the internal chamber. An adjustable stop positioned in the internal chamber selectively adjusts the amount of force exerted by the biasing member on the float.

12 Claims, 7 Drawing Sheets

(56) References Cited

U.S. PATENT DOCUMENTS

| | | |
|---|---|---|
| 8,025,054 B2 | 9/2011 | Dunsmore |
| 8,251,876 B2 | 8/2012 | Boerst |
| 8,327,849 B2 | 12/2012 | Foley |
| 8,534,284 B2 | 9/2013 | Dunsmore |
| 8,758,202 B2 | 6/2014 | Foley |
| 8,783,251 B2 | 7/2014 | Koledin |
| 2003/0140925 A1 | 7/2003 | Sapienza |
| 2010/0206310 A1* | 8/2010 | Matsubara ......... A61M 16/208 128/205.24 |
| 2012/0012111 A1* | 1/2012 | Howe, Jr. ......... A61M 16/1055 128/205.12 |
| 2012/0041329 A1 | 2/2012 | Chatham |
| 2012/0186585 A1 | 7/2012 | Richards |
| 2012/0272956 A1 | 11/2012 | Rusher |
| 2013/0228174 A1 | 9/2013 | Guo |

* cited by examiner

POSITIVE EXPIRATORY PRESSURE DEVICE AND METHODS OF USING SAME

CROSS-REFERENCE TO RELATED APPLICATIONS

This application claims the benefit of and priority to U.S. Provisional Patent 62/037,569, filed Aug. 14, 2014, which is incorporated in its entirety in this document by reference.

FIELD OF THE INVENTION

This invention relates generally to a positive expiratory pressure device and methods of using same, and more specifically, a hand-held positive expiratory pressure device for assisting pulmonary functions of a user.

BACKGROUND OF THE INVENTION

Positive expiratory pressure ("PEP") occurs when there is positive pressure present in the lungs of a person during exhalation. Typically, this positive expiratory pressure can be created by pursing one's own lips (for example, after exercising to help catch your breath). Positive expiratory pressure therapy is a clinically recognized treatment for persons having chronic obstructive pulmonary disease (COPD), chronic bronchitis, cystic fibrosis, atelectasis, or other conditions resulting in collapsed alveoli and which might in turn produce retained secretions in the lungs. During this therapy, positive expiratory pressure can be created during exhalation with a PEP device.

With PEP therapy, a patient exhales against a resistance created by the PEP device to generate expiratory pressure. Conventionally, therapeutic PEP devices are designed and utilized in a hospital or home environment because conventional therapeutic PEP devices are relatively large and/or need a power source to function. Thus, a patient desiring PEP therapy cannot always get treatment when needed. What is needed then is a PEP device and method to create positive expiratory pressure that can be small enough to be carried with a user and is discreet to use.

SUMMARY

Presented herein are positive expiratory pressure (PEP) devices and methods of using same. In one aspect, the PEP device comprises at least one of: a housing, a float, a stop, a top and a biasing member. In use, the float can be positioned in an internal chamber of the housing in contact with a sealing surface of the housing. The biasing member can urge the float towards the sealing surface. When a user of the PEP device exhales into a mouthpiece of the housing, the expiratory air pressure can urge the float away from the sealing surface creating the desired positive expiratory pressure.

In one aspect, the housing has an open first end, an open second end and a sidewall defining the internal chamber. In another aspect, at least one axial rib can extend from the sidewall into a portion of the internal chamber. The sealing surface can be formed in a portion of the internal chamber of the housing.

The top can be rotatably attachable to the open second end of the housing. A proximal end of the top can be configured to be inserted into a portion of the internal chamber of the housing. In one aspect, at least a portion of the proximal end of the top can be threaded to complementarily engage threads defined in a portion of the stop.

The stop has a distal face, a proximal face and at least one stop sidewall extending therebetween. In one aspect, the stop can be sized and shaped to fit into at least a portion of the internal chamber of the housing. In another aspect, at least one axial notch can be defined in a portion of the stop sidewall, the at least one axial notch configured to matingly engage the at least one axial rib of the housing. That is, upon alignment of the axial notch of the stop and the axial rib of the housing, the stop can slide axially along the rib but can be prevented from rotating relative to the housing. In a further aspect, a central aperture that extends from the distal face to the proximal face can be defined in the stop. At least a portion of the central aperture can be threaded to matingly engage the thread of the top.

The float can be sized and shaped to fit into at least a portion of the internal chamber of the housing. In one aspect, the float comprises a plug and an elongate shaft extending away from the plug. In another aspect, the plug can have a sealing face configured to matingly engage at least a portion of the sealing surface of the housing to prevent and/or restrict the passage of a fluid between the sealing surface and the sealing face. In another aspect, the plug can have a second face that is opposed to the sealing face.

The biasing member can be, for example and without limitation, a compressive spring configured to be positioned between a portion of the second face of the float and the proximal face of the stop. In use, the spring can urge the float away from the stop and towards the sealing surface of the housing. In one aspect, the force exerted by the spring on the float and the stop can be the resistance a user of the PEP device must overcome to create the desired positive expiratory pressure.

To assemble the PEP device, the float can be can be positioned in the internal chamber of the housing. The spring can be positioned on the second face of the float. The stop can be positioned in the internal chamber between the spring and the second end of the housing. The at least one axial notch of the stop can be aligned with the at least one axial rib of the housing such that the stop can slide axially therein the internal chamber. At least a portion of the proximal end of the top can be inserted through the central aperture of the stop so that the at least one thread of the top can matingly engage the thread of the stop. A distal end of the top can rotatably engage the second end of the housing so that the top can rotate relative to the housing.

In use, a user can rotate the top relative to the housing to a desired orientation. Rotation of the top can cause the thread of the top to engage the thread of the stop and move the stop axially relative to the housing and the float. Thus, rotation of the top can selectively vary the distance between the proximal face of the stop and the second face of the float, and thus vary the amount of compression on the spring. The position of the proximal face of the stop relative to the second face of the float can be adjusted to selective increase or decrease the force exerted by the spring on the float and thus the amount of resistance created by the PEP device. The user can then place his lips on a mouthpiece of the housing and exhale. Expiratory air pressure can urge the float away from the sealing surface of the housing and toward the stop.

Other apparatuses, methods, systems, features, and advantages will be or become apparent to one with skill in the art upon examination of the following figures and detailed description. It is intended that all such additional apparatuses, methods, systems, features, and advantages be included within this description, be within the scope of the devices and methods for creating positive expiratory pressure, and be protected by the accompanying claims.

DESCRIPTION OF THE FIGURES

The accompanying drawings, which are incorporated in and constitute a part of this specification, illustrate certain aspects of the instant invention and together with the description, serve to explain, without limitation, the principles of the invention Like reference characters used therein indicate like parts throughout the several drawings.

DESCRIPTION OF THE INVENTION

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "port" includes aspects having two or more ports unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Terms used herein, such as "exemplary" or "exemplified," are not meant to show preference, but rather to explain that the aspect discussed thereafter is merely one example of the aspect presented.

Figure 1:
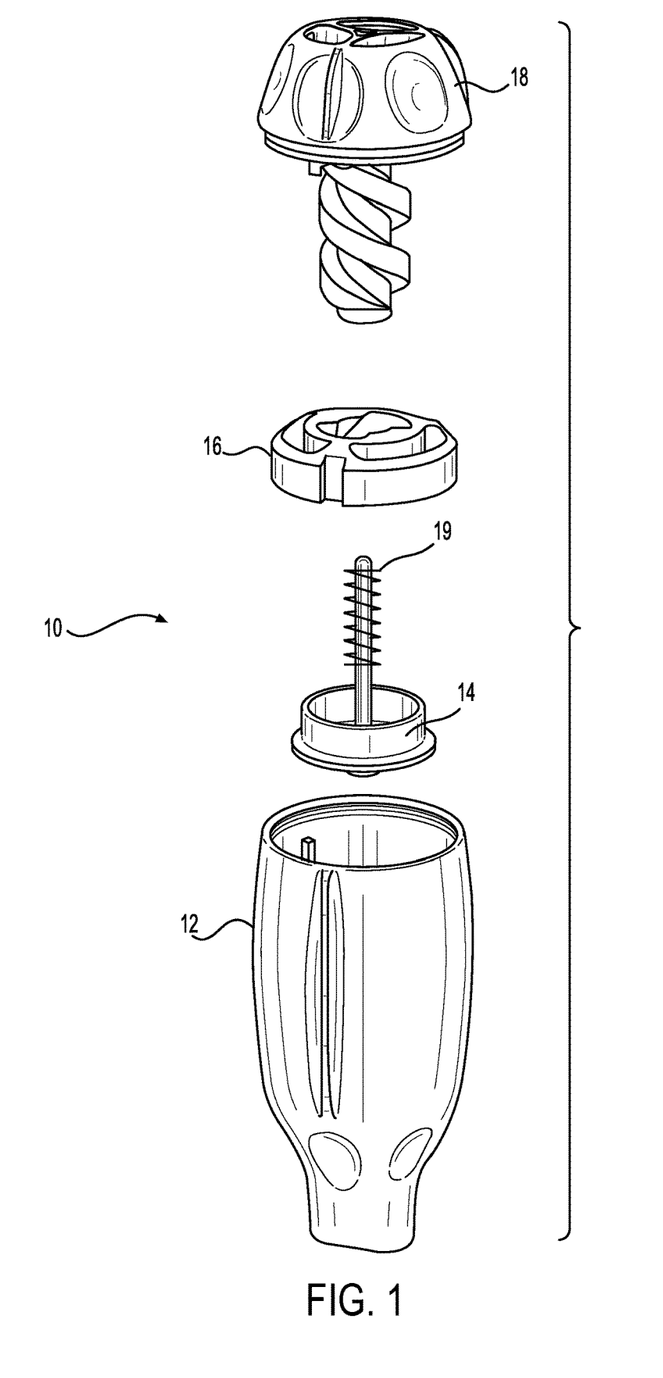
FIG. 1 is an exploded perspective view of a positive expiratory pressure device comprising a housing, a float, a stop and a top, according to one aspect.

Presented herein are positive expiratory pressure (PEP) devices and methods of using same. With reference to FIG. 1, the PEP device 10 comprises at least one of: a housing 12, a float 14, a stop 16, a top 18 and a biasing member 19. In use, the float can be positioned in an internal chamber of the housing with the biasing member such that when a user exhales into a mouthpiece of the housing, the expiratory air pressure can overcome the force exerted on the float 14 by the biasing member to create positive expiratory pressure.

Figure 2A:
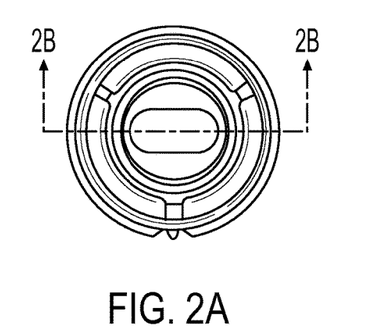
FIGS. 2A, 2B and 2C are an end view, a cross-sectional view, and a perspective view of the housing of FIG. 1.
Figure 2B:
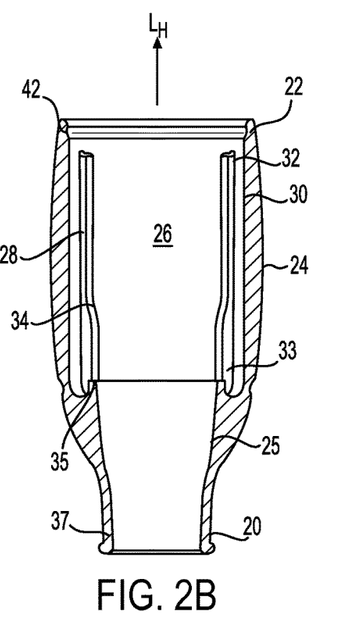
Figure 2C:
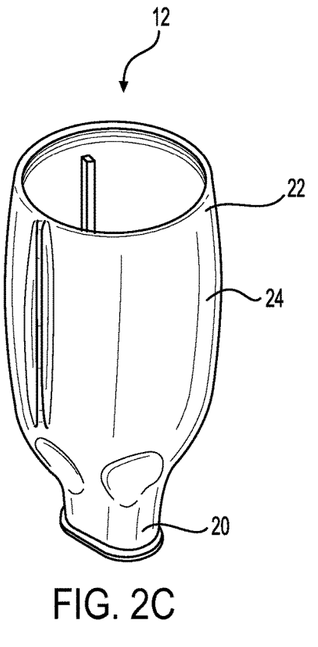

In one aspect and as illustrated in FIGS. 2A-2C, the housing 12 has a longitudinal axis $L_H$, an open first end 20, an open second end 22 opposed to the first end and a sidewall 24 extending between the first end and the second end. The first end 20, the second end 22 and the sidewall cooperate to define an internal chamber 26. In this aspect, the internal chamber of the housing 12 can be configured to contain at least a portion of the float 14 and/or the stop 16 therein. In another aspect, at least one axial rib 28 configured to position the float and/or the stop in a desired position therein the internal chamber can extend from an inner surface 30 of the sidewall 24 into the internal chamber 26. At least a portion of the axial rib can be substantially parallel to the longitudinal axis $L_H$ of the housing 12. In a further aspect, at least a portion of the at least one axial rib 28 can be spaced from the inner surface 30 of the sidewall 24 a predetermined distance such that a distal end 32 of the rib can be selectively biased towards or away from the inner surface 30. In yet another aspect, a shoulder 34 configured to engage a portion of the float 14 and/or the stop 16 can be formed on at least one axial rib 28. In use, the shoulder can extend into the internal chamber 26 a predetermined distance beyond the axial rib to prevent or restrict the float and/or the stop from sliding axially along the rib beyond the shoulder.

A sealing surface 35 can be formed in a portion of the internal chamber 26 of the housing. In one aspect, the sealing surface can be an annular sealing surface. In this aspect, the sealing surface can be positioned near or adjacent to the proximal end 33 of the at least one axial rib. In another aspect, the sealing surface 35 can be substantially planar. Optionally, the sealing surface can be substantially transverse to the longitudinal axis $L_H$ of the housing 12. The sealing surface 35 can be configured to matingly engage a portion of the float 14 to prevent or restrict the passage of a fluid between the sealing surface and the float.

In another aspect, the open first end 20 of the housing 12 can be sized and shaped to form a mouthpiece 37. For example, the open first end can be configured such that the lips of a user can fit around at least a portion of the first end and that exhaled fluid from the user can travel through the open first end 20 and into the internal chamber 26 of the housing 12. In one aspect, an internal diameter 25 of the sidewall 24 can become greater in a direction from the first end 20 towards the second end 22 of the housing. That is, the internal diameter of the internal chamber 26 can increase when moving along a portion of the internal chamber in a direction from the first end towards the second end. For example, the internal diameter 25 of the internal chamber can increase from the first end until a proximal end 33 of the axial rib. Optionally, the internal diameter of the internal chamber can be substantially constant between the proximal end 33 and the distal end 32 of the axial rib 28.

Figure 3:
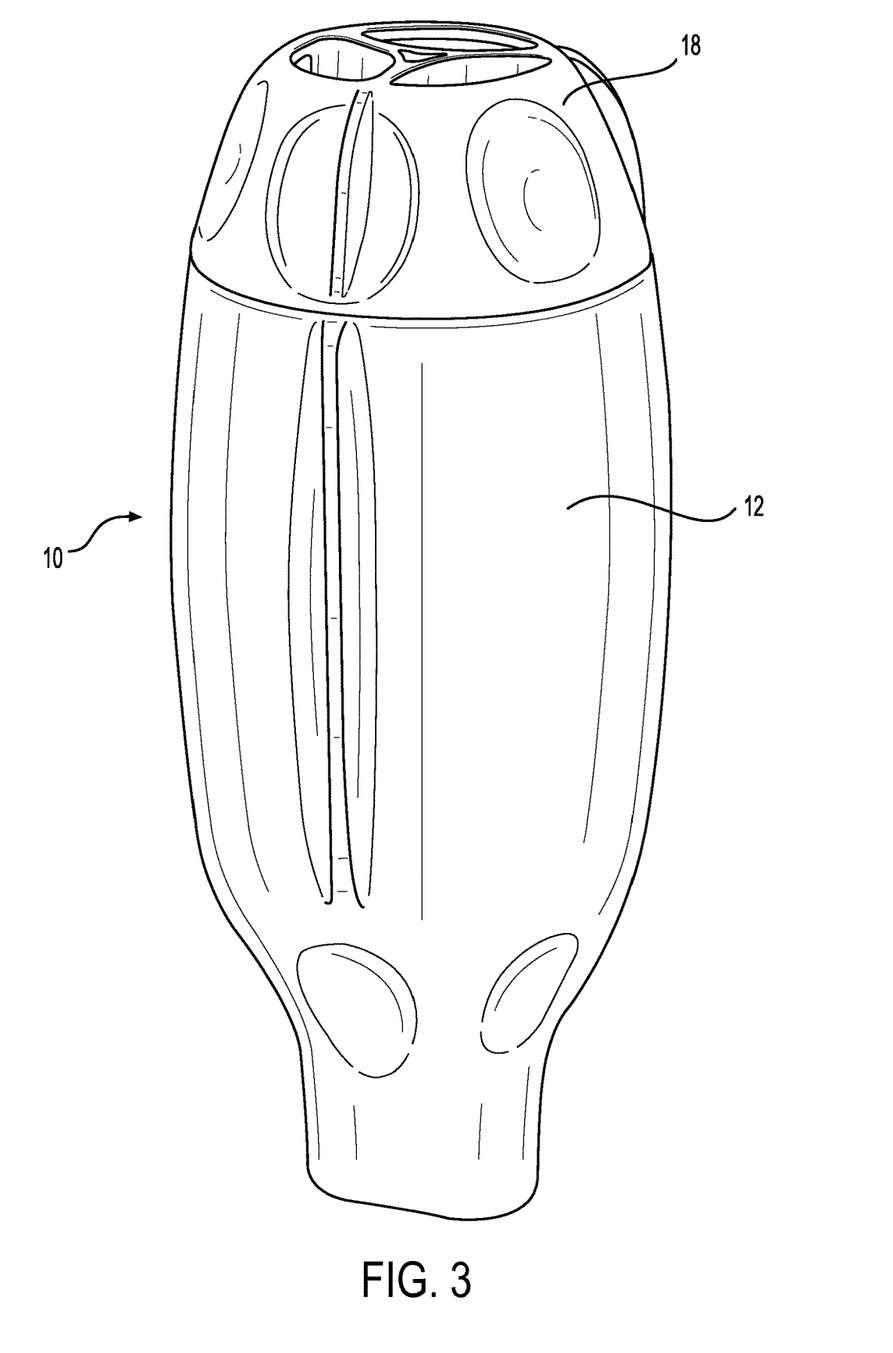
FIG. 3 is a perspective view of the assembled positive expiratory pressure device of FIG. 1.
Figure 4A:
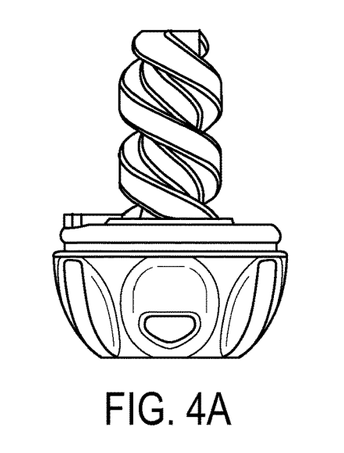
FIGS. 4A, 4B, 4C and 4D are an elevational view, an end view, a cross-sectional view, and a perspective view of the top of FIG. 1.
Figure 4B:
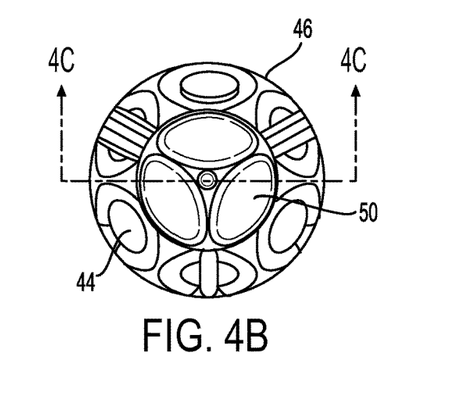
Figure 4C:
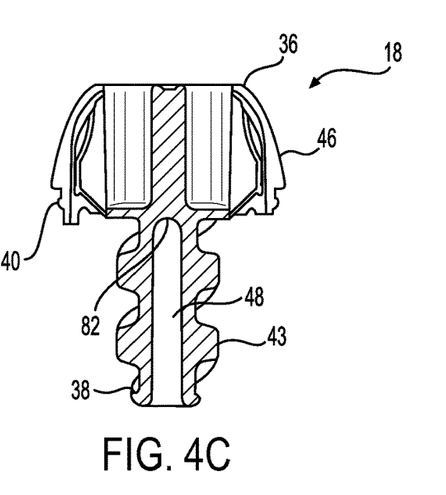
Figure 4D:
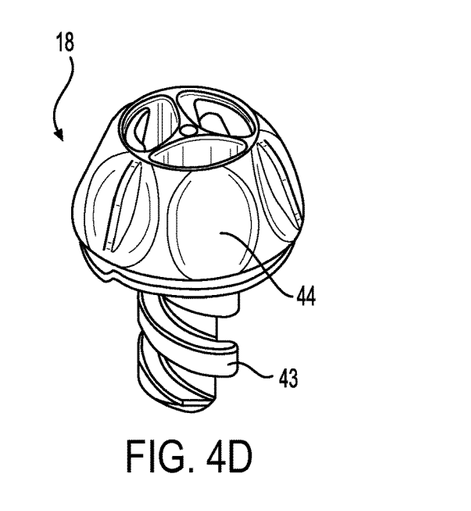

Referring now to FIGS. 2A and 3, the open second end 22 of the housing 12 can be configured to matingly engage a portion of the top 18. For example, the top can be snap-fit into the open second end. In one aspect, the top can be rotatably attached to the second end 22. That is, in this aspect, the top 18 can be rotatable relative to the housing 12. In another aspect, the top can rotate about a rotation axis that is parallel to the longitudinal axis $L_H$ of the housing. In yet another aspect, the top 18 can at least partially enclose and/or seal the open second end 22 of the housing.

The top 18 is illustrated in FIGS. 4A-4D, according to one aspect. The top has a distal end 36 and an opposed proximal end 38. The distal end of the top 18 can be configured to engage the second end 22 of the housing, as discussed above. For example, an annular ring 40 formed around at least a portion of the distal end of the top can be configured to engage an annular groove 42 defined in the housing. Alternatively, it is contemplated that the annular ring can be formed on the housing 12 and the annular groove can be defined in the top 18. In another aspect, at least one gripping notch 44 can be defined in an outer surface 46 of the distal end 36 of the top 18. The gripping notch can be configured so that a user can easily rotate the top relative to the housing 12.

The proximal end 38 of the top 18 can be configured to be inserted into a portion of the internal chamber 26 of the housing 12. Thus, the diameter of the proximal end of the top can be less than the diameter of the distal end 36 of the top 18. In one aspect, at least one thread 43 can be defined in a portion of the proximal end of the top 18. In use, described more fully below, at least a portion of the proximal end 38 of the top can be threaded to complementarily engage threads defined in a portion of the stop 16. In another aspect, an elongate bore 48 can be defined in a portion of the proximal end 38 of the top. In this aspect, the elongate bore can be sized and shaped to receive a portion of the float 14 therein. As will be described more fully below, the elongate bore 48 can be configured so that as the float moves axially in the internal chamber 26, the top will not undesirably restrict movement of the float. Optionally, the elongate bore 48 can be configured so that as the float 14 moves axially in the internal chamber, the top 18 prevents movement of a portion of the float more than a predetermined distance away from the sealing surface 35 of the housing 12.

At least one port 50 can be defined in the distal end 36 of the top 18, according to one aspect. In this aspect, the at least one port can be configured so that fluid can pass through the port 50 and thus through the top. For example, when the top 18 is positioned on the second end 22 of the housing, fluid can pass through the internal chamber 26, into the top, and through the at least one port 50 of the top 18 to the atmosphere. In another aspect, the at least one port can comprises a plurality of ports. In yet another aspect, the plurality of ports 50 can be substantially evenly sized and/or spaced relative to each other. Optionally, however, the plurality of ports can be unevenly sized and/or unevenly spaced relative to each other.

Figure 5A:
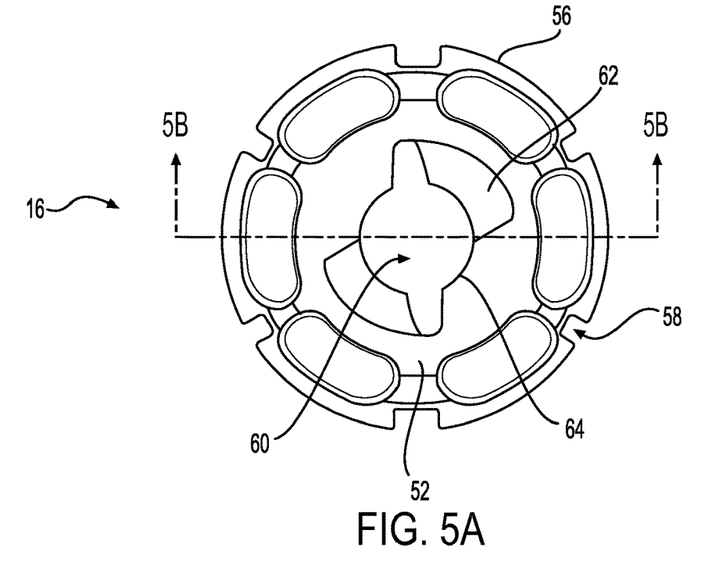
FIGS. 5A, 5B and 5C are an end view, a cross-sectional view, and a perspective view of the stop of FIG. 1.
Figure 5B:
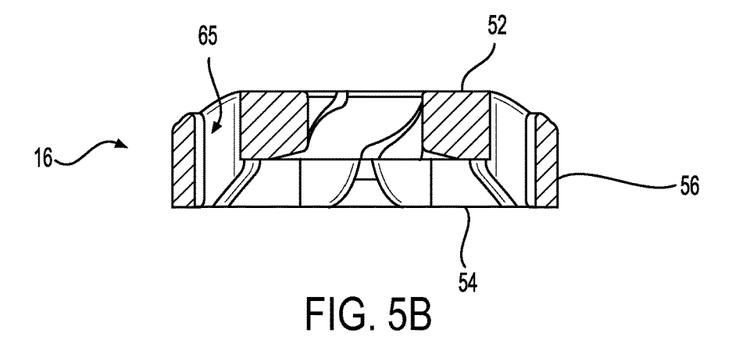
Figure 5C:
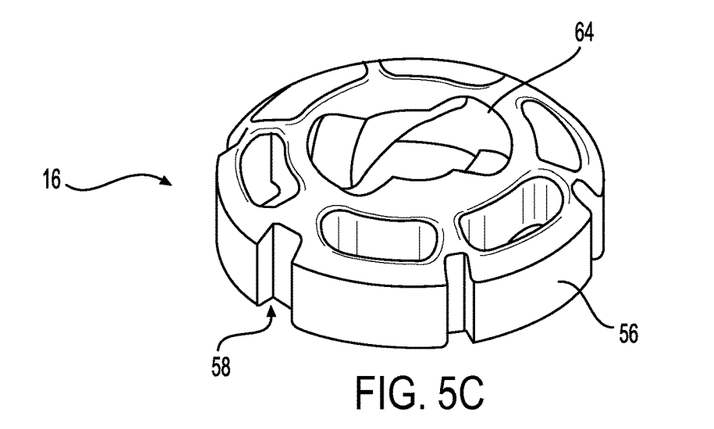
Figure 7:
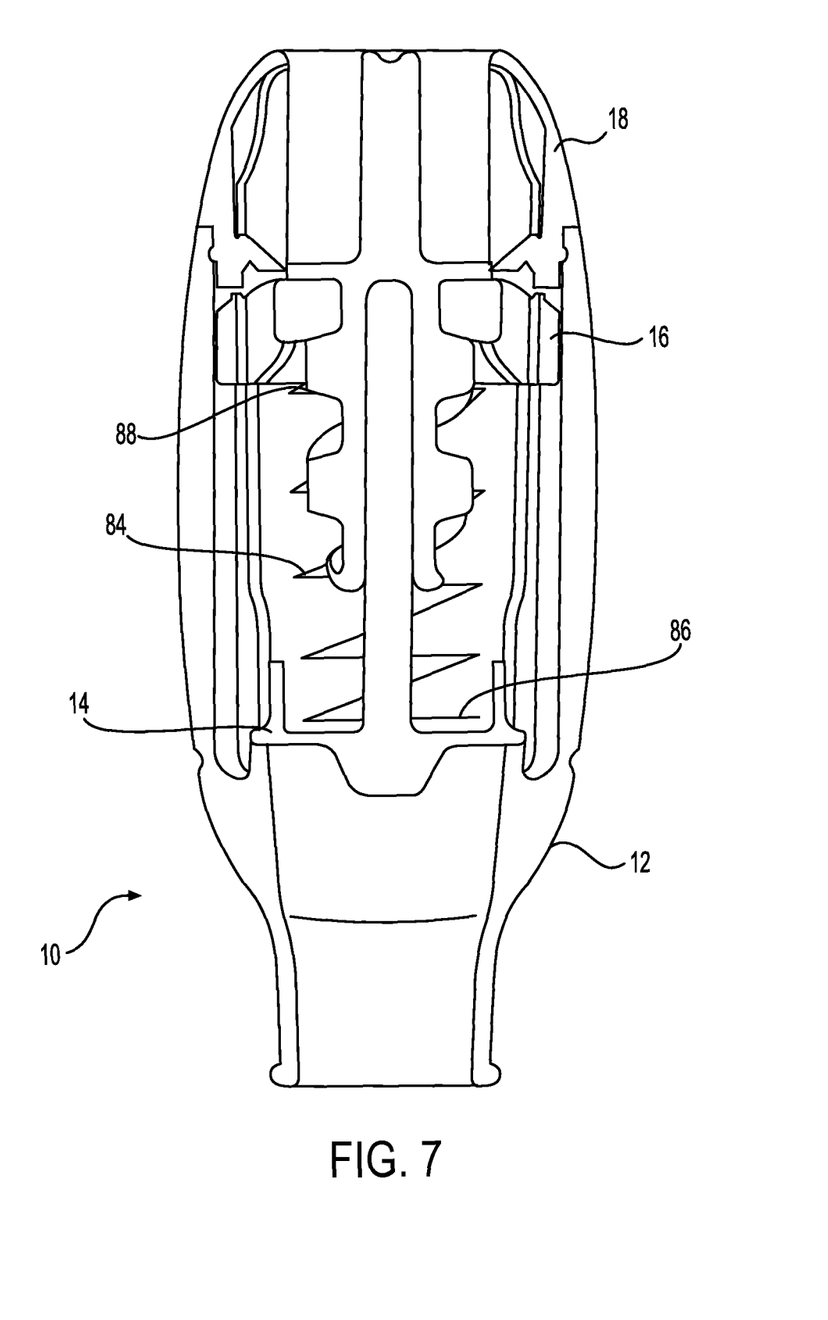
FIG. 7 is a cross-sectional view of the assembled positive expiratory pressure device of FIG. 1.

The stop 16 is illustrated in FIGS. 5A-5C, according to one aspect. The stop has a distal face 52, a proximal face 54 and at least one stop sidewall 56 extending therebetween. In one aspect, the stop 16 can be sized and shaped to fit into at least a portion of the internal chamber 26 of the housing 12 (as illustrated in FIG. 7). For example, the stop can have an outer perimeter dimension that is less the diameter of the internal chamber so that the stop can be inserted at least partially into the internal chamber 26. In another aspect, the proximal face 54 of the stop 16 can engage the distal end 32 of the at least one axial rib 28 of the internal chamber.

In one aspect, at least one axial notch 58 extending from the distal face 52 to the proximal face 54 of the stop 16 can be defined in a portion of the stop sidewall 56. In this aspect, the at least one axial notch can be configured to matingly engage the at least one axial rib 28 of the housing 12. For example, the stop 16 can be rotated relative to the housing so that the at least one notch is substantially aligned with the at least one axial rib and the stop can be positioned in the internal chamber 26 in the desired position. In this aspect, the mating engagement of the at least one axial rib 28 and the at least one axial notch 58 can prevent or restrict rotation of the stop relative to the housing while allowing the stop 16 to move axially relative to the housing 12. In another aspect, the at least one notch can comprises a plurality of notches 58. In a further aspect, the plurality of notches can be substantially evenly sized and/or spaced relative to each other. Optionally, however, the plurality of notches 58 can be unevenly sized and/or unevenly spaced relative to each other.

In one aspect, a central aperture 60 that extends from the distal face 52 to the proximal face 54 can be defined in the stop 16. The central aperture can be sized and shaped to engage a portion of the proximal end 38 of the top 18. In one aspect, at least one thread 62 can be defined in at least a portion of an aperture wall 64 of the central aperture. That is, the at least one thread 62 of the stop 16 can extend at least partially along the aperture wall between the distal face 52 and the proximal face 54 of the stop 16. In use, described more fully below, the thread 62 of the stop can matingly engage the thread 43 of the top 18 such that, upon rotation of the top relative to the housing 12, the mating threads of the stop 16 and the top can urge the stop axially (substantially parallel to the longitudinal axis $L_H$ of the housing). In another aspect, at least one stop port 65 that extends from the distal face 52 of the stop 16 to the proximal face 54 can be defined in the stop 16. In this aspect, the stop port 65 can be configured to place the distal face and the proximal face of the stop in fluid communication when the PEP device 10 is assembled.

Figure 6A:
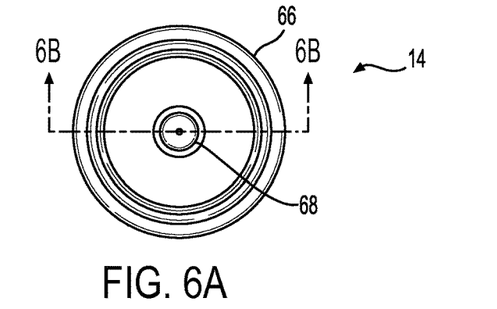
FIGS. 6A, 6B and 6C are an end view, a cross-sectional view, and a perspective view of the float of FIG. 1.
Figure 6B:
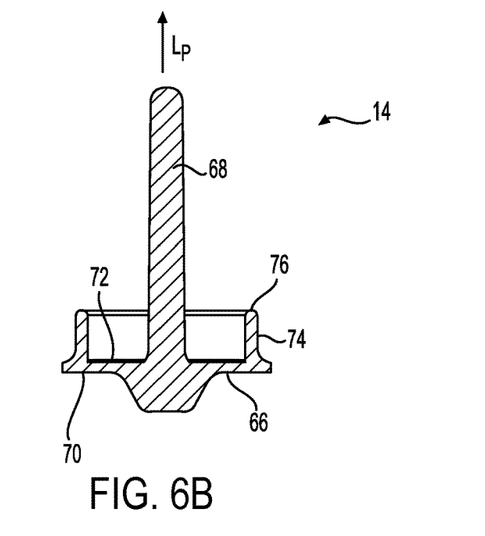
Figure 6C:
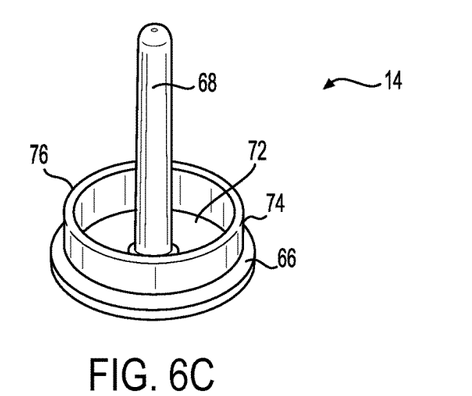

The float 14 is illustrated in FIGS. 6A-6C, according to one aspect. The float can be sized and shaped to fit into at least a portion of the internal chamber 26 of the housing 12 (as illustrated in FIG. 7). For example, the float 14 can have an outer diameter that is less than the diameter of the internal chamber so that the float can be inserted at least partially into the internal chamber 26. In one aspect, the float comprises a plug 66 and an elongate shaft 68. The elongate shaft can extend away from the plug along a longitudinal axis $L_P$. In another aspect, the plug can have a sealing face 70 configured to matingly engage a portion on the housing 12. For example, the sealing face can be configured to matingly engage at least a portion of the sealing surface 35 of the housing to prevent or restrict the passage of a fluid between the sealing surface and the sealing face 70 of the float 14. In use, described more fully below, the float 14 can be movable about and between a first, closed position, in which the sealing face 70 of the plug 66 can engage the sealing surface 35 of the housing 12 to prevent the flow of fluid through the internal chamber and a second open position, in which the sealing face of the plug is spaced from the sealing surface of the housing a predetermined distance to allow fluid to flow through the housing. In one aspect, at least a portion of the sealing face 70 can be substantially planar. Optionally, at least a portion of the sealing face can be substantially transverse to the longitudinal axis $L_P$ of the elongate shaft 68.

In one aspect, the plug 66 can have a second face 72 that is opposed to the sealing face 70. At least one float sidewall 74 can extend from the second face a predetermined wall distance and end at a stopping surface 76. In another aspect, at least a portion of the second face and/or the stopping surface can be substantially planar. Optionally, at least a portion of the second face 72 and/or the stopping surface 76 can be in a plane substantially transverse to the longitudinal axis $L_P$ of the shaft 68. In yet another aspect, at least a portion of the second face and/or the stopping surface can be substantially parallel to the sealing face 70.

In one aspect, the elongate shaft 68 has a proximal end 78 coupled to or formed integrally with the second face 72 of the plug 66, and a distal end 80 spaced from the second face of the plug a predetermined shaft distance. The elongate shaft 68 of the float 14 can be sized and shaped to fit within the biasing member 19, such as, for example and without limitation, a spring 84. In another aspect, the elongate shaft can be sized and shaped to be insertable into the bore 48 of the top 18. In this aspect, the predetermined shaft distance can be selected so that, when the PEP device 10 is assembled, the distal end 80 of the elongate shaft 68 does not contact an end wall 82 of the bore 48 of the top when the sealing face 70 of the float 14 is in a desired position relative to the sealing surface 35 of the housing 12. For example, when the sealing face 70 of the float 14 is spaced from the sealing surface 35 of the housing 12 a predetermined spacing distance, the distal end 80 of the elongate shaft 68 does not contact the end wall of the bore. Optionally, the predetermined shaft distance can be selected so that, when the PEP device 10 is assembled, the distal end 80 of the elongate shaft 68 contacts the end wall 82 of the bore 48 when the sealing face of the float is in a desired position relative to the sealing surface 35 of the housing 12. In another aspect, the elongate shaft can be substantially concentric with the at least one float sidewall 74.

With reference to FIGS. 1 and 7, the biasing member 19 can be for example and without limitation, a spring 84 configured to be positioned between a portion of the float 14 and the stop 16. In another aspect, a first end 86 of the spring can be positioned on or engage a portion of the second face 72 of the float, and a second end 88 of the spring 84 can be positioned on or engage a portion of the proximal face 54 of the stop. The spring can have an internal diameter greater than an outer diameter of the elongate shaft 68 of the float 14 and greater than an outer diameter of the proximal end 38 of the top 18 so that the spring can be positioned around at least a portion of the elongate shaft and the proximal end of the top. In one aspect, the spring 84 can be, for example and without limitation, a compressive spring configured to urge the float 14 and the stop 16 away from each other. In one aspect, the force exerted by the spring on the float and the stop can be the resistance a user of the PEP device 10 must overcome to create the desired positive expiratory pressure.

To assemble the PEP device 10, the float 14 can be can be positioned in the internal chamber 26 of the housing 12 between the first end 20 and the second end 22 such that at least a portion of the sealing face 70 engages the sealing surface 35 of the housing. The spring 84 can be positioned around the elongate shaft 68 of the float such that the first end 86 of the spring is positioned on a portion of the second face 72 of the float 14. The stop 16 can be positioned in the internal chamber between the float and the second end such that the at least one axial notch 58 of the stop is substantially aligned with the at least one axial rib 28 of the housing 12. Upon alignment of the notch of the stop 16 with the rib of the housing, the stop can slide axially (in a direction substantially parallel to the longitudinal axis $L_H$ of the housing) until the proximal face 54 of the stop contacts the second end 88 of the spring 84. At least a portion of the proximal end 38 of the top 18 can be inserted through the aperture 60 of the stop 16 so that the at least one thread 43 of the top can matingly engage the thread 62 of the stop. In this position, optionally, at least a portion of the elongate shaft 68 of the float 14 can be positioned therein the elongate bore 48 of the top 18. The distal end 36 of the top 18 can engage the second end 22 of the housing 12 with, for example and without limitation, a snap fit, as discussed above so that the top 18 can rotate relative to the housing. Optionally, a lanyard hole can be defined in a portion of the housing 12 and/or the top 18 so that a lanyard can be attached to the PEP device 10 and a user can have the device nearby without having to look for it. Note that, the lanyard hole would not be in fluid communication with the internal chamber 26 of the housing. The assembled PEP device 10 can be small enough to fit into a hand of the user. Optionally, the assembled PEP device can be small enough to discreetly fit into a hand of the user so that the presence of the device is not obvious.

In use, a user can selectively rotate the top 18 relative to the housing 12 to a desired position. Rotation of the top can rotate the at least one thread 43 of the top. Because the thread 43 of the top can matingly engage the thread 62 of the stop 16, rotation of the top can move the stop axially (in a direction substantially parallel to the longitudinal axis $L_H$ of the housing). For example, rotation of the top 18 in a first direction can cause the stop to move axially towards the first end 20 of the housing until the proximal face 54 of the stop contacts a portion of the shoulder 34 of the axial rib 28, until the proximal face of the stop 16 contacts a portion of the stopping surface 76 of the float 14 and/or until the spring 84 is fully compressed. In another example, rotation of the top in a second direction that is opposed to the first direction can cause the stop 16 to move axially towards the second end 22 of the housing 12 until the distal face 52 of the stop contacts a portion of the top. Thus, rotation of the top 18 can cause the stop to move axially relative to the float such that the distance between the proximal face 54 of the stop and the second face 72 of the float 14 can be varied about and between a first gap distance (that can be zero inches or greater than zero inches) and a second gap distance that is greater than the first gap distance. That is, the stop can be movable about and between a first stop position, in which the stop is positioned a first predetermined distance from the first end 20 of the housing 12, and a second stop position, in which the stop 16 is positioned a second predetermined distance from the first end of the housing that is less than the first predetermined distance.

Because the biasing member 19 can be positioned in the area between the proximal face 54 of the stop 16 and the second face 72 of the float, any change in the gap distance can change the amount of force exerted by the biasing member on the float 14. For example, when the stop is positioned at the first gap distance, the spring 84 can be fully compressed and can exert a relatively large force on the float. In another example, when the stop 16 is at the second gap distance, the spring 84 can be less than fully compressed and can exert a relatively smaller force on the float 14. That is, with the stop 16 in the first stop position, the biasing member 19 can exert a first force on the float, and with the stop in the second stop position, the biasing member can exert a second force on the float that is greater than the first force.

The user can then place his lips on the mouthpiece 37 of the housing 12 and exhale. If the expiratory air pressure is greater than the force exerted by the spring 84 on the float 14, the expiratory air pressure can urge the float away from the sealing surface 35 of the housing 12 so that exhaled fluid can flow between the sealing surface and the float (and then between the outer diameter of the float and the inner surface 30 of the sidewall 24) through the internal chamber 26, through the at least one stop port 65 of the stop 16, through the at least one port 50 of the top and out of the PEP device 10. If the expiratory air pressure from the user is less than the force exerted by the spring 84 on the float, the float will not move and the exhaled fluid will not be able to flow between the sealing surface 35 and the float 14. As can be appreciated then, the position of the proximal face 54 of the stop relative to the stopping surface 76 of the float 14 (the gap distance) can be adjusted to selectively increase or decrease the force exerted by the spring 84 on the float 14 and thus the amount of resistance created by the PEP device. For example, the user can rotate the top 18 to a second position which moves the stop 16 to a second position. This can cause the spring 84 to exert a smaller force on the float so that the expiratory air pressure can be greater than the force exerted by the spring 84 on the float.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. A positive expiratory pressure device comprising:
   a housing having an open first end, an open second end and a sidewall extending between the open first end and the open second end, wherein the open first end, the open second end and the sidewall cooperate to define an internal chamber, and wherein a sealing surface is formed in a portion of the internal chamber;
   a top attached to the open second end of the housing, the top having a distal end and a proximal end, wherein the top at least partially encloses the open second end, and wherein at least one port is defined in the top such that fluid can pass through the port and into the internal chamber of the housing;
   a stop having a distal face, a proximal face and a stop sidewall extending between the distal face and the proximal face, wherein at least a portion of the stop is positioned in the internal chamber of the housing between the distal end of the top and the open first end of the housing, and wherein at least one stop port is defined in the stop such that the distal face and the proximal face of the stop are in fluid communication;
   a float comprising a plug positioned in at least a portion of the internal chamber of the housing between the stop and the open first end of the housing, wherein the plug has a sealing face configured to matingly engage the sealing surface of the housing; and
   a biasing member positioned in the internal chamber of the housing between the plug and the stop, wherein the biasing member urges the sealing face of the plug toward the sealing surface of the housing,
   wherein the float is movable about and between a first, closed position, in which the sealing face of the plug of the float engages the sealing surface of the housing to prevent the flow of fluid through the internal chamber, and a second open position, in which the sealing face of the plug is spaced from the sealing surface of the housing a predetermined distance to allow fluid to flow through the housing, and wherein in use, when a user exhales into the open first end of the housing, the plug is movable from the first closed position to the second open position to create positive expiratory pressure, and wherein the at least one thread of the stop matingly engages the at least one thread of the top such that, upon selective rotation of the top relative to the housing by a user, the mating threads of the stop and the top move the stop axially relative to the housing.

2. The device of claim 1, wherein the sealing surface is an annular sealing surface.

3. The device of claim 1, wherein the open first end of the housing is configured to form a mouthpiece.

4. The device of claim 1, wherein the housing has a longitudinal axis, wherein the housing comprises at least one axial rib extending from an inner surface of the sidewall of the housing into the internal chamber, and wherein at least a portion of the axial rib is substantially parallel to the longitudinal axis of the housing.

5. The device of claim 4, wherein the top is rotatably attached to the open second end of the housing such that the top is rotatable about a rotation axis that is parallel to the longitudinal axis of the housing.

6. The device of claim 5, wherein the distal end of the top is rotatably attached to the open second end of the housing and wherein the proximal end of the top is inserted into a portion of the internal chamber of the housing.

7. The device of claim 6, wherein at least one thread can be defined in a portion of the proximal end of the top.

8. The device of claim 7, wherein at least one axial notch is defined in at least a portion of the stop sidewall, wherein the at least one axial notch is configured to matingly engage the at least one axial rib of the housing, and wherein the mating engagement of the at least one axial rib and the at least one axial notch prevents rotation of the stop relative to the housing while allowing the stop to move axially relative to the housing.

9. The device of claim 8, wherein a central aperture is defined in a portion of the stop, wherein at least one thread is defined in at least a portion of an aperture wall of the central aperture.

10. The device of claim 1, wherein the stop is movable about and between a first stop position, in which the stop is positioned a first predetermined distance from the open first end of the housing, and a second stop position, in which the stop is positioned a second predetermined distance from the open first end of the housing that is less than the first predetermined distance.

11. The device of claim 10, wherein in the first stop position, the biasing member exerts a first force on the float, and wherein in the second stop position, the biasing member exerts a second force on the float that is greater than the first force.

12. The device of claim 11, wherein the device is sized to be portable and held in the hand of the user.

* * * * *